US008329408B2

(12) United States Patent
Wilhelm

(10) Patent No.: US 8,329,408 B2
(45) Date of Patent: Dec. 11, 2012

(54) METHODS FOR PROGNOSIS AND MONITORING CANCER THERAPY

(75) Inventor: Scott Wilhelm, Milford, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 11/589,295

(22) Filed: Oct. 30, 2006

(65) Prior Publication Data

US 2007/0105142 A1    May 10, 2007

Related U.S. Application Data

(60) Provisional application No. 60/731,278, filed on Oct. 31, 2005.

(51) Int. Cl.
*G01N 33/53* (2006.01)

(52) U.S. Cl. ........................................... 435/7.1

(58) Field of Classification Search ........................ None
See application file for complete search history.

(56) References Cited

U.S. PATENT DOCUMENTS

| | | | | |
|---|---|---|---|---|
| 2003/0232400 | A1* | 12/2003 | Radka et al. | 435/7.23 |
| 2006/0234931 | A1* | 10/2006 | Biggs et al. | 514/12 |
| 2007/0020704 | A1* | 1/2007 | Wilhelm et al. | 435/7.21 |

FOREIGN PATENT DOCUMENTS

| | | |
|---|---|---|
| WO | WO 03/097854 A2 * | 11/2003 |
| WO | 2005/089442 A2 | 9/2005 |

OTHER PUBLICATIONS

Wilhelm et al (Cancer Research, Oct. 2004, 64:7099-7109).*
Reilly et at (J Nucl Med, May 2000, 41(5):903-911).*
Elting et al (Proceedings of the American Association for Cancer Resarch, vol. 47, Apr. 2006; cited in IDS submitted with the Reply of May 1, 2008).*
Ahmad et al (Clin. Can. Res. vol. 10: 6388s-6392s).*
Wilhelm et al (Cancer Research, Oct. 2004, 64: 7099-7109).*
Tockman et al (Cancer Res., 1992, 52:2711s-2718s).*
Murphy et al., "BAY 43-9006 Controls Tumor Growth Though Inhibition of Vascular Development," 96th Annual Meeting, Anaheim/Orange County, CA Apr. 16-20, 2005.
Elting et al., XP001245679, #2909 Biomarkers Associated With Clinical Outcomes in TARGETs, a Phase III Single-Agent, Placebo-Controlled Study of Sorafenib in Advanced Renal Cell Carcinoma; Proceedings of the American Association for Cancer Research, vol. , 7, Apr. 2006.
DePrimo et al., Circulating Protein Biomarkers of Pharmacodynamic Activity of Sunitinib in Patients With Metastatic Renal Cell Carcinoma: Modulation of VEGF and VEGF-Related Proteing; Journal of Translational Medicine, Jul. 2, 2007, pp. 1-11.
Ahmad et al., XP-00236266, Kinase Inhibition With BAY 43-9006 Renal Cell Carcinoma, Clinical Cancer Research, vol. 10, 6388s-6392s, Sep. 15, 2004.
Veronese et al., XP001249174, Mechanisms of Hypertension Associated With BAY-43-9006, Journal of Clinical Oncology, vol. 24, No. 9, Mar. 20, 2006.
Foekens et al., XP-002425575, High Tumor Levels of Vascular Endothelial Growth Factor Predict Poor Response to Systemic Therapy in Advanced Breast Cancer, Cancer Research 61, 5407-5414, Jul. 15, 2001.
XP-002425577, Journal Article, mRNA Expression of the Angiogenesis Markers VEGF and CD105 (endoglin) in Human Breast Cancer, Anticancer Research, Greece May-Jun. 2004.

* cited by examiner

*Primary Examiner* — Sean Aeder
(74) *Attorney, Agent, or Firm* — Millen, White, Zelano & Branigan, P.C.

(57) ABSTRACT

The present invention also relates to biomarkers and the use of biomarkers for the prediction and prognosis of cancer as well as the use of biomarkers to monitor the efficacy of cancer treatment. Specifically, this invention relates to the use of HER-2, EGFR, VEGF, u-PA, p-PAI-1, and soluble forms thereof, as biomarkers for cancer, especially for subjects treated with sorafenib.

4 Claims, No Drawings

METHODS FOR PROGNOSIS AND MONITORING CANCER THERAPY

This application claims the benefit of the filing date of U.S. Provisional Application Ser. No. 60/731,278 filed Oct. 31, 2005, the entire disclosure of which is incorporated by reference herein.

FIELD OF THE INVENTION

The present invention relates to biomarkers and the use of biomarkers for the prediction and prognosis of cancer as well as the use of biomarkers to monitor the efficacy of cancer treatment. Specifically, this invention relates to the use of HER-2, EGFR, VEGF, u-PA (urokinase-plasminogen activator), p-PAI-1, and soluble forms thereof, as biomarkers as biomarkers for cancer.

BACKGROUND OF THE INVENTION

Many disease states are characterized by differences in the expression levels of various genes either through changes in the copy number of the genetic DNA or through changes in levels of transcription of particular genes (e.g., through control of initiation, provision of RNA precursors, RNA processing, etc.). For example, losses and gains of genetic material play an important role in malignant transformation and progression. These gains and losses are thought to be driven by at least two kinds of genes, oncogenes and tumor suppressor genes. Oncogenes are positive regulators of tumorgenesis, while tumor suppressor genes are negative regulators of tumorgenesis (Marshall, Cell 64:313-326, 1991; Weinberg, Science 254:1138-1146, 1991). Therefore, one mechanism of activating unregulated growth is to increase the number of genes coding for oncogene proteins or to increase the level of expression of these oncogenes (e.g., in response to cellular or environmental changes), and another mechanism is to lose genetic material or to decrease the level of expression of genes that code for tumor suppressors. This model is supported by the losses and gains of genetic material associated with glioma progression (Mikkelson, et al., J. Cellular Biochem. 46:3-8, 1991). Thus, changes in the expression (transcription) levels of particular genes (e.g., oncogenes or tumor suppressors) serve as signposts for the presence and progression of various cancers.

DESCRIPTION OF THE INVENTION

The present invention relates to biomarkers and the use of biomarkers for the prediction and prognosis of cancer as well as the use of biomarkers to monitor the efficacy of cancer treatment. Specifically, this invention relates to the use of HER-2, EGFR, VEGF, u-PA (urokinase-plasminogen activator), p-PAI-1, and soluble forms thereof, as biomarkers for cancer (including both solid tumors, metastatic tumors, and blood cancers), such as breast cancer, colon carcinoma, melanoma, renal cell carcinoma, non-small cell lung cancer, acute myeloid leukemia, and myelodyspastic syndrome, and hepatocellular cancer, especially for subjects treated with sorafenib and other diarylureas.

In addition, it is an objective of the invention to provide methods and reagents for the prediction, diagnosis, prognosis, and therapy of cancer.

In one embodiment of the present invention, the biomarkers comprise one or more genes and/or gene products that demonstrate altered expression following exposure to sorafenib and other diarylureas.

Sorafenib is the tosylate salt of 4-{4-[({[4-Chloro-3-(trifluoromethyl)phenyl]amino}carbonyl)amino]phenoxy}-N-methylpyridine-2-carboxamide. The synthesis and use of 4-{4-[({[4-Chloro-3-trifluoromethyl)phenyl]amino}carbonyl)amino]phenoxy}-N-methylpyridine-2-carboxamide and many other ureas, as well as pharmaceutically acceptable salts thereof such as tosylate salts, are described in a number of applications including international applications WO 00/42012, WO 00/41698, WO 02/062763, WO 03/354,950, WO 02/085859, WO 03/047579 and WO 04/15653, which are incorporated herein by reference.

An example of a procedure to synthesize N-[4-chloro-3-(trifluoromethyl)phenyl]-N'-{4-[2-carbamoyl-1-oxo-(4-pyridyloxy)]phenyl}urea follows:

Step 1: Preparation of 4-chloro-2-pyridinecarboxamide

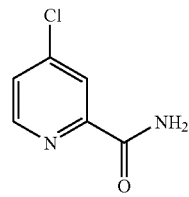

To a stirred mixture of methyl 4-chloro-2-pyridinecarboxylate hydrochloride (1.0 g, 4.81 mmol) dissolved in conc. aqueous ammonia (32 mL) is added ammonium chloride (96.2 mg, 1.8 mmol, 0.37 equiv.), and the heterogeneous reaction mixture is stirred at ambient temperature for 16 h. The reaction mixture is poured into EtOAc (500 mL) and water (300 mL). The organic layer is washed with water (2×300 mL) and a saturated NaCl solution (1×300 mL), dried (MgSO$_4$), concentrated in vacuo to give 4-chloro-2-pyridinecarboxamide as a beige solid (604.3 mg, 80.3%): TLC (50% EtOAc/hexane) R$_f$ 0.20; $^1$H-NMR (DMSO-d$_6$) □ 8.61 (d, J=5.4 Hz, 1H), 8.20 (broad s, 1H), 8.02 (d, J=1.8 Hz, 1H), 7.81 (broad s, 1H), 7.76 to 7.73 (m, 1H).

Step 2: Preparation of 4-(4-aminophenoxy)-2-pyridinecarboxamide

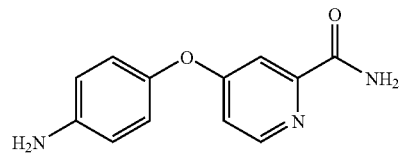

To 4-aminophenol (418 mg, 3.83 mmol) in anh DMF(7.7 mL) is added potassium tert-butoxide (447 mg, 3.98 mmol, 1.04 equiv.) in one portion. The reaction mixture is stirred at room temperature for 2 h, and a solution of 4-chloro-2-pyridinecarboxamide (600 mg, 3.83 mmol, 1.0 equiv.) in anh DMF (4 mL) is then added. The reaction mixture is stirred at 80° C. for 3 days and poured into a mixture of EtOAc and a saturated NaCl solution. The organic layer is sequentially washed with a saturated NH$_4$Cl solution then a saturated NaCl solution, dried (MgSO$_4$), and concentrated under reduced pressure. The crude product is purified using MPLC chromatography (Biotage®; gradient from 100% EtOAc to followed by 10% MeOH/50% EtOAc/40% hexane) to give the 4-chloro-5-trifluoromethylaniline as a brown solid (510 mg, 58%). $^1$H-NMR (DMSO-$d_6$) ☐ 8.43 (d, J=5.7 Hz, 1H), 8.07 (br s, 1H), 7.66 (br s, 1H), 7.31 (d, J=2.7 Hz, 1H), 7.07 (dd, J=5.7 Hz, 2.7 Hz, 1H), 6.85 (d, J=9.0 Hz, 2 H), 6.62 (d, J=8.7 Hz, 2H), 5.17 (broad s, 2H); HPLC EI-MS m/z 230 ((M+H)$^+$.

Step 3: Preparation of N-[4-chloro-3-(trifluoromethyl)phenyl]-N'-{4-[2-carbamoyl-(4-pyridyloxy)]phenyl}urea

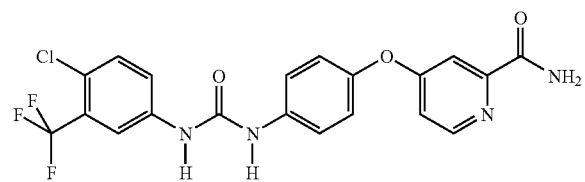

A mixture of 4-chloro-5-trifluoromethylaniline (451 mg, 2.31 mmol, 1.1 equiv.) and 1,1'-carbonyl diimidazole (419 mg, 2.54 mmol, 1.2 equiv.) in anh dichloroethane (5.5 mL) is stirred under argon at 65° C. for 16 h. Once cooled to room temperature, a solution of 4-(4-aminophenoxy)-2-pyridinecarboxamide (480 mg, 2.09 mmol) in anh THF (4.0 mL) is added, and the reaction mixture is stirred at 60° C. for 4 h. The reaction mixture is poured into EtOAc, and the organic layer is washed with water (2×) and a saturated NaCl solution (1×), dried (MgSO$_4$), filtered, and evaporated in vacuo. Purification using MPLC chromatography (Biotage®; gradient from 100% EtOAc to 2% MeOH/EtOAc) gave N-[4-chloro-3-(trifluoromethyl)phenyl]-N'-{4-[2-carbamoyl-(4-pyridyloxy)]phenyl}urea as a white solid (770 mg, 82%): TLC (EtOAc) R$_f$ 0.11, 100% ethyl acetate $^1$H-NMR (DMSO-$d_6$) ☐ 9.21 (s, 1H), 8.99 (s, 1H), 8.50 (d, J=5.6 Hz, 1H), 8.11 (s, 1H), 8.10 (s, 1H), 7.69 (broad s, 1H), 7.64 (dd, J=8.2 Hz, 2.1 Hz, 1H), 7.61 (s, 1H), 7.59 (d, J=8.8 Hz, 2H), 7.39 (d, J=2.5 Hz, 1H), 7.15 (d, J=8.9 Hz, 2H), 7.14 (m, 1H); MS LC-MS (MH$^+$=451). Anal. calcd for $C_{20}H_{14}ClF_3N_4O_3$: C, 53.29%; H, 3.13%; N, 12.43%. Found: C, 53.33%; H, 3.21%; N, 12.60%.

Another method of preparing N-[4-chloro-3-(trifluoromethyl)phenyl]-N'-{4-[2-carbamoyl-(4-pyridyloxy)]phenyl}urea are described in Bankston et al. "A Scaleable Synthesis of BAY 43-9006: A Potent Raf Kinase Inhibitor for the Treatment of Cancer" Org. Proc. Res. Dev. 2002, 6(6), 777-781.

The formation of pharmaceutically acceptable salts such as tosylate salts from these ureas can be performed by conventional methods. An example of the preparation of sorafenib, the tosylate salt of 4-{4-[({[4-Chloro-3-(trifluoromethyl)phenyl]amino}carbonyl)amino]phenoxy}-N-methylpyridine-2-carboxamide, in the polymorph II is as follows:

903 g of 4-{4-[({[4-chloro-3-(trifluoromethyl)phenyl]amino}carbonyl)amino]phenoxy}-N-methylpyridine-2-carboxamide, prepared as described above, are initially charged in 2700 ml of ethanol. 451.7 g of p-toluenesulfonic acid monohydrate are dissolved in 1340 g of ethanol and added dropwise at room temperature. The suspension is stirred at room temperature for 1 hour, then filtered off with suction, and the residue is washed three times with 830 ml each time of ethanol. The drying is effected at 50° C. under reduced pressure with supply of air. 1129.6 g of the tosylate salt of 4-{4-[({[4-Chloro-3-(trifluoromethyl)phenyl]amino}carbonyl)amino]phenoxy}-N-methylpyridine-2-carboxamide in the polymorph II are obtained.

An example of the preparation of sorafenib, 4-{4-[({[4-chloro-3-(trifluoromethyl)phenyl]amino}carbonyl)-amino]phenoxy}-N-methylpyridine-2-carboxamide tosylate, in the polymorph I is as follows:

Heating 5 mg of sorafenib, [tosylate salt of 4-{4-[({[4-chloro-3-(trifluoromethyl)phenyl]amino}carbonyl)amino]-phenoxy}-N-methylpyridine-2-carboxamide] in the polymorph II to 200° C. at a heating rate of 20° C./min and subsequently cooling to room temperature at a cooling rate of 2° C./min. The sample is tested thermoanalytically (DSC) and corresponds to the title compound in the polymorph I.

Methods for preparing the compounds of this invention are also described in the following U.S. applications:.
Ser. No. 09/425,228, filed Oct. 22, 1999;
Ser. No. 09/722,418 filed Nov. 28, 2000
Ser. No. 09/758,547, filed Jan. 12, 2001;
Ser. No. 09/838,285, filed Apr. 20, 2001;
Ser. No. 09/838,286, filed Apr. 20, 2001; and The entire disclosure of all applications, patents and publications cited above and below including copending application Ser. No. 10/308,187 filed Dec. 12, 2002 and Ser. No. 10/848,567 filed May 19, 2004, are hereby incorporated by reference.

Another embodiment of the present invention is a method for screening the effects of a drug on a tissue or cell sample comprising the step of analyzing the level of expression of one or more genes and/or gene products, wherein the gene expression and/or gene product levels in the tissue or cell sample are analyzed before and after exposure to the drug, and a variation in the expression level of the gene and/or gene product is indicative of a drug effect or provides a patient diagnosis or predicts a patient's response to the treatment. In a further embodiment, the drug is sorafenib and/or- other diarylureas. In another embodiment, the gene or gene product is HER-2, EGFR, VEGF, u-PA, p-PAI-1, and soluble forms thereof, e.g., as detected in tumor tissue, lymph, and/or blood, especially blood serum.

Another aspect of the present invention is a method for discovering novel drugs comprising the step of analyzing the level of expression of one or more genes and/or gene products, wherein the gene expression and/or gene product levels of the cells are analyzed before and after exposure to the drug, and a variation in the expression level of the gene and/or gene product is indicative of drug efficacy. In a further aspect, the gene or gene product is In another embodiment, the gene or gene product is HER-2, EGFR, VEGF, u-PA, p-PAI-1, and soluble forms thereof, e.g., as detected in tumor tissue, lymph, and/or blood, especially blood serum.

The invention further provides a method for identifying a compound useful for the treatment of cancer comprising administering to a subject with cancer a test compound, and measuring the activity of the polypeptide, wherein a change in the activity of the polypeptide is indicative of the test compound being useful for the treatment of cancer. In a further embodiment, the polypeptide is In another embodiment, the gene or gene product is HER-2, EGFR, VEGF, u-PA, p-PAI-1, and soluble forms thereof, e.g., as detected in tumor tissue, lymph, and/or blood, especially blood serum, and in another embodiment, the compound is a sorafenib or another diarylurea.

The invention, thus, provides methods which may be used to identify compounds which may act, for example, as regulators or modulators such as agonists and antagonists, partial agonists, inverse agonists, activators, co-activators, and inhibitors. Accordingly, the invention provides reagents and methods for regulating the expression of a polynucleotide or a polypeptide associated with cancer. Reagents that modulate the expression, stability, or amount of a polynucleotide or the activity of the polypeptide may be a protein, a peptide, a peptidomimetic, a nucleic acid, a nucleic acid analogue (e.g., peptide nucleic acid, locked nucleic acid), or a small molecule.

The present invention also provides a method for providing a patient diagnosis comprising the step of analyzing the level of expression of one or more genes and/or gene products, wherein the gene expression and/or gene product levels of normal and patient samples are analyzed, and a variation in the expression level of the gene and/or gene product in the patient sample is diagnostic of a disease. The patient samples include, but are not limited to, blood, amniotic fluid, plasma, semen, bone marrow, and tissue biopsy. In a further embodiment, the gene or gene product is HER-2, EGFR, VEGF, u-PA, p-PAI-1, and soluble forms thereof, e.g., as detected in tumor tissue, lymph, and/or blood, especially blood serum.

The present invention still further provides a method of diagnosing cancer in a subject comprising measuring the activity of the polypeptide in a subject suspected of having cancer, wherein if there is a difference in the activity of the polypeptide, relative to the activity of the polypeptide in a subject not suspected of having cancer, then the subject is diagnosed has having cancer. In a further embodiment, the polypeptide is HER-2, EGFR, VEGF, u-PA, p-PAI-1, and soluble forms thereof, e.g., as detected in tumor tissue, lymph, and/or blood, especially blood serum.

In another embodiment, the invention provides a method for detecting cancer in a patient sample in which an antibody to a protein is used to react with proteins in the patient sample. In a still further embodiment, the antibody is specific for HER-2, EGFR, VEGF, u-PA, p-PAI-1, and soluble forms thereof, e.g., as detected in tumor tissue, lymph, and/or blood, especially blood serum.

Another aspect of the present invention is a method for distinguishing between normal and disease states comprising the step of analyzing the level of expression of one or more genes and/or gene products, wherein the gene expression and/or gene product levels of normal and disease tissues are analyzed, and a variation in the expression level of the gene and/or gene product is indicative of a disease state. In a further aspect, the gene or gene product is HER-2, EGFR, VEGF, u-PA, p-PAI-1, and soluble forms thereof, e.g., as detected II tumor tissue, lymph, and/or blood, especially blood serum.

In another embodiment, the invention pertains to a method of determining the phenotype of cells comprising detecting the differential expression, relative to normal cells, of at least one gene, wherein the gene is differentially expressed by at least a factor of two, at least a factor of five, at least a factor of twenty, or at least a factor of fifty. In a further embodiment, the gene encodes HER-2, EGFR, VEGF, u-PA, p-PAI-1, and soluble forms thereof.

Any test sample in which it is desired to identify a polynucleotide or polypeptide thereof can be used, including, e.g., blood, urine, saliva, stool (for extracting nucleic acid, see, e.g., U.S. Pat. No. 6,177,251), swabs comprising tissue, biopsied tissue, tissue sections, cultured cells, etc.

Detection can be accomplished in combination with polynucleotide probes for other genes, e.g., genes which are expressed in other disease states, tissues, cells, such as brain, heart, kidney, spleen, thymus, liver, stomach, small intestine, colon, muscle, lung, testis, placenta, pituitary, thyroid, skin, adrenal gland, pancreas, salivary gland, uterus, ovary, prostate gland, peripheral blood cells (T-cells, lymphocytes, etc.), embryo, normal breast fat, adult and embryonic stem cells, specific cell-types, such as endothelial, epithelial, myocytes, adipose, luminal epithelial, basoepithelial, myoepithelial, stromal cells, etc.

In yet another embodiment, the invention pertains to a method of determining the phenotype of cells, comprising detecting the differential expression, relative to normal cells, of at least one polypeptide, wherein the protein is differentially expressed by at least a factor of two, at least a factor of five, at least a factor of twenty, an up to at least a factor of fifty. In a further embodiment, the polypeptide is HER-2, EGFR, VEGF, u-PA, and p-PAI-1.

In another embodiment, the invention pertains to a method for determining the phenotype of cells from a patient by providing a nucleic acid probe comprising a nucleotide sequence having at least about 10, at least about 15, at least about 25, or at least about 40 consecutive nucleotides, obtaining a sample of cells from a patient, optionally providing a second sample of cells substantially all of which are non-cancerous, contacting the nucleic acid probe under stringent conditions with mRNA of each of said first and second cell samples, and comparing (a) the amount of hybridization of the probe with mRNA of the first cell sample, with (b) the amount of hybridization of the probe with mRNA of the second cell sample, wherein a difference of at least a factor of two, at least a factor of five, at least a factor of twenty, or at least a factor of fifty in the amount of hybridization with the mRNA of the first cell sample as compared to the amount of hybridization with the mRNA of the second cell sample is indicative of the phenotype of cells in the first cell sample. In a further embodiment, the nucleic acid probe comprises the nucleotide sequence encoding HER-2, EGFR, VEGF, u-PA, p-PAI-1, and soluble forms thereof.

In another embodiment, the invention provides a test kit for identifying the presence of cancerous cells or tissues, comprising a probe/primer, for measuring a level of a nucleic acid in a sample of cells or serum isolated from a patient. In certain embodiments, the kit may further include instructions for using the kit, solutions for suspending or fixing the cells, detectable tags or labels, solutions for rendering a nucleic acid susceptible to hybridization, solutions for lysing cells, or solutions for the purification of nucleic acids. In a further embodiment, the probe/primer comprises the nucleotide sequence encoding HER-2, EGFR, VEGF, u-PA, p-PAI-1, and soluble forms thereof, e.g., as detected in tumor tissue, lymph, and/or blood, especially blood serum.

In one embodiment, the invention provides a test kit for identifying the presence of cancer cells or tissues, comprising an antibody specific for a protein. In certain embodiments, the kit further includes instructions for using the kit. In certain embodiments, the kit may further include solutions for suspending or fixing the cells, detectable tags or labels, solutions for rendering a polypeptide susceptible to the binding of an antibody, solutions for lysing cells, or solutions for the purification of polypeptides. In a still further embodiment, the antibody is specific for HER-2, EGFR, VEGF, u-PA, p-PAI-1, and soluble forms thereof.

In another embodiment, the invention provides a test kit for monitoring the efficacy of a compound or therapeutic in cancerous cells or tissues, comprising a probe/primer, for measuring a level of a nucleic acid hi a sample isolated from a patient. In certain embodiments, the kit may further include instructions for using the kit, solutions for suspending or fixing the cells, detectable tags or labels, solutions for rendering a nucleic acid susceptible to hybridization, solutions for lysing cells, or solutions for the purification of nucleic acids. In a further embodiment, the probe/primer comprises the nucleotide sequence encoding HER-2, EGFR, VEGF, u-PA, p-PAI-1, and soluble forms thereof, e.g., as detected hi tumor tissue, lymph, and/or blood, especially blood serum.

In one embodiment, the invention provides a test kit for monitoring the efficacy of a compound or therapeutic in cancer cells, tissues.

It is to be understood that this invention is not limited to the particular methodology, protocols, cell lines, animal species or genera, constructs, and reagents described and as such may vary. It is also to be understood that the terminology used herein is for the purpose of describing C particular embodiments only, and is not intended to limit the scope of the present invention which will be limited only by the appended claims.

It must be noted that as used herein and in the appended claims, the singular forms "a," "and," and "the" include plural reference unless the context clearly dictates otherwise. Thus, for example, reference to "a gene" is a reference to one or more genes and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used hi the practice or testing of the invention, the preferred methods, devices and materials are now described.

All publications and patents mentioned herein are hereby incorporated herein by reference for the purpose of describing and disclosing, for example, the constructs and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Definitions

For convenience, the meaning of certain terms and phrases employed in the specification, examples, and appended claims are provided below.

An "address" on an array (e.g., a microarray) refers to a location at which an element, for example, an oligonucleotide, is attached to the solid surface of the array.

The term "agonist," as used herein, is meant to refer to an agent that mimics or up-regulates (e.g., potentiates or supplements) the bioactivity of a protein. An agonist may be a wild-type protein or derivative thereof having at least one bioactivity of the wild-type protein. An agonist may also be a compound that up-regulates expression of a gene or which increases at least one bioactivity of a protein. An agonist can also be a compound which increases the interaction of a polypeptide with another molecule, for example, a target peptide or nucleic acid.

"Amplification," as used herein, relates to the production of additional copies of a nucleic acid sequence. For example, amplification may be carried out using polymerase chain reaction (PCR) technologies which are well known in the art. (see, e.g., Dieffenbach and Dveksler (1995) PCR Primer, A Laboratory Manual, Cold Spring Harbor Press, Plainview, N.Y.)

The term "antibody," as used herein, is intended to include whole antibodies, for example, of any isotype (IgG, IgA, IgM, IgE, etc.), and includes fragments thereof which are also specifically reactive with a vertebrate (e.g., mammalian) protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal, human, single chain, humanized, and other antibody types and recombinant antibodies.

The terms "array" or "matrix" refer to an arrangement of addressable locations or "addresses" on a device. The locations can be arranged in two-dimensional arrays, three-dimensional arrays, or other matrix formats. The number of locations may range from several to at least hundreds of thousands. Most importantly, each location represents a totally independent reaction site. A "nucleic acid array" refers to an array containing nucleic acid probes, such as oligonucleotides or larger portions of genes. The nucleic acid on the array is preferably single-stranded. Arrays wherein the probes are oligonucleotides are referred to as "oligonucleotide arrays" or "oligonucleotide chips." A "microarray," also referred to herein as a "biochip" or "biological chip," is an array of regions having a density of discrete regions of at least about 100/cm$^2$, and preferably at least about 1000/cm$^2$. The regions in a microarray have typical dimensions, for example, diameters, in the range of between about 10-250 μm, and are separated from other regions in the array by about the same distance.

"Biological activity" or "bioactivity" or "activity" or "biological function," which are used interchangeably, herein mean an effector or antigenic function that is directly or indirectly performed by a polypeptide (whether in its native or denatured conformation), or by any subsequence thereof. Biological activities include binding to polypeptides, binding to other proteins or molecules, activity as a DNA binding protein, as a transcription regulators ability to bind damaged DNA, etc. A bioactivity can be modulated by directly affecting the subject polypeptide. Alternatively, a bioactivity can be altered by modulating the level of the polypeptide, such as by modulating expression of the corresponding gene.

The term "biological sample," as used herein, refers to a sample obtained from an organism or from components (e.g., cells) of an organism. The sample may be of any biological tissue or fluid. The sample may be a sample which is derived from a patient. Such samples include, but are not limited to, sputum, blood, blood cells (e.g., white blood cells), tissue or biopsy samples (e.g., tumor biopsy), urine, peritoneal fluid, and pleural fluid, or cells therefrom. Biological samples may also include sections of tissues such as frozen sections taken for histological purposes.

The term "biomarker" or "marker" encompasses a broad range of intra- and extra-cellular events as well as whole-organism physiological changes. Biomarkers may be represent essentially any aspect of cell function, for example, but not limited to, levels or rate of production of signaling molecules, transcription factors, metabolites, gene transcripts as well as post-transactional modifications of proteins. Biomarkers may include whole genome analysis of transcript levels or whole proteome analysis of protein levels and/or modifications.

A biomarker may also refer to a gene or gene product which is up- or down-regulated in a compound-treated, diseased cell of a subject having the disease compared to an untreated diseased cell. That is, the gene or gene product is sufficiently specific to the treated cell that it may be used, optionally with other genes or gene products, to identify, predict, or detect efficacy of a small molecule. Thus, a biomarker is a gene or gene product that is characteristic of efficacy of a compound in a diseased cell or the response of that diseased cell to treatment by the compound.

A nucleotide sequence is "complementary" to another nucleotide sequence if each of the bases of the two sequences match, that is, are capable of forming Watson-Crick base pairs. The term "complementary strand" is used herein interchangeably with the term "complement." The complement of a nucleic acid strand may be the complement of a coding strand or the complement of a non-coding strand.

"Detection agents of genes" refers to agents that can be used to specifically detect the gene or other biological molecules relating to it, for example, RNA transcribed from the gene or polypeptides encoded by the gene. Exemplary detection agents are nucleic acid probes, which hybridize to nucleic acids corresponding to the gene, and antibodies.

Baseline levels can refer to a standard control for "normal" levels (i.e., patients without disease), but can also be comparative, e.g., where low baseline levels is compared to the levels of other subjects having the disease.

The term "cancer" includes, but is not limited to, solid tumors, such as cancers of the breast, respiratory tract, brain, reproductive organs, digestive tract, urinary tract, eye, liver, skin, head and neck, thyroid, parathyroid, and their distant metastases. The term also includes lymphomas, sarcomas, and leukemias.

Examples of breast cancer include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumor.

Tumors of the male reproductive organs include, but are not limited to, prostate and testicular cancer. Tumors of the female reproductive organs include, but are not limited to, endometrial, cervical, ovarian, vaginal, and vulvar cancer, as well as sarcoma of the uterus.

Tumors of the digestive tract include, but are not limited to, anal, colon, colorectal, esophageal, gallbladder, gastric, pancreatic, rectal, small-intestine, and salivary gland cancers.

Tumors of the urinary tract include, but are not limited to, bladder, penile, kidney, renal pelvis, ureter, and urethral cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignianit melanoma, Merkel cell skin cancer, and non-melanoma skin cancer.

Head-and-neck cancers include, but are not limited to, laryngeal/hypopharyngeal/nasopharyngeal/oropharyngeal cancer, and lip and oral cavity cancer.

Lymphomas include, but are not limited to, AIDS-related lymphoma, non-Hodgkin's lymphoma, cutaneous T-cell lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

"A diseased cell of cancel" refers to a cell present in subjects having cancer. That is, a cell which is a modified form of a normal cell and is not present in a subject not having cancer, or a cell which is present in significantly higher or lower numbers in subjects having cancer relative to subjects not having cancer.

The term "equivalent" is understood to include nucleotide sequences encoding functionally equivalent polypeptides. Equivalent nucleotide sequences may include sequences that differ by one or more nucleotide substitutions, additions, or deletions, such as allelic variants.

The term "expression profile," which is used interchangeably herein with "gene expression profile" and "fingerprint" of a cell refers to a set of values representing mPNA levels of one or more genes in a cell. An expression profile preferably comprises values representing expression levels of at least about 10 genes, preferably at least about 50, 100, 200 or more genes. Expression profiles may also comprise an mRNA level of a gene which is expressed at similar levels in multiple cells and conditions (e.g., a housekeeping gene such as GAPDH). For example, an expression profile of a diseased cell of cancer refers to a set of values representing mRNA levels of 10 or more genes in a diseased cell.

The term "gene" refers to a nucleic acid sequence that comprises control and coding sequences necessary for the production of a polypeptide or precursor. The polypeptide can be encoded by a full length coding sequence or by any portion of the coding sequence. The gene may be derived in whole or in part from any source known to the art, including a plant, a fungus, an animal, a bacterial genome or episome, eukaryotic, nuclear or plasmid DNA, cDNA, viral DNA, or chemically synthesized DNA. A gene may contain one or more modifications in either the coding or the untranslated regions which could affect the biological activity or the chemical structure of the expression product, the rate of expression, or the manner of expression control. Such modifications include, but are not limited to, mutations, insertions, deletions, and substitutions of one or more nucleotides. The gene may constitute an uninterrupted coding sequence or it may include one or more introns, bound by the appropriate splice junctions.

"Hybridization" refers to any process by which a strand of nucleic acid binds with a complementary strand through base pairing. For example, two single-stranded nucleic acids "hybridize" when they form a double-stranded duplex. The region of double-strandedness may include the full-length of one or both of the single-stranded nucleic acids, or all of one single-stranded nucleic acid and a subsequence of the other single-stranded nucleic acid, or the region of double-strandedness may include a subsequence of each nucleic acid. Hybridization also includes the formation of duplexes which contain certain mismatches, provided that the two strands are still forming a double-stranded helix. "Stringent hybridization conditions" refers to hybridization conditions resulting in essentially specific hybridization.

The term "isolated," as used herein, with respect to nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, culture medium when produced by recombinant DNA techniques, or chemical precursors or other chemicals when chemically synthesized. Moreover, an "isolated nucleic acid" may include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

As used herein, the terms "label" and "detectable label" refer to a molecule capable of detection, including, but not limited to, radioactive isotopes, fluorophores, chemiluminescent moieties, enzymes, enzyme substrates, enzyme cofactors, enzyme inhibitors, dyes, metal ions, ligands (e.g., biotin or haptens), and the like. The term "fluorescer" refers to a substance or a portion thereof which is capable of exhibiting fluorescence in the detectable range. Particular examples of labels which may be used in the present invention include fluorescein, rhodamine, dansyl, umbelliferone, Texas red, luminol, NADPH, alpha- beta-galactosidase, and horseradish peroxidase.

As used herein, the term "level of expression" refers to the measurable expression level of a given nucleic acid. The level of expression of a nucleic acid is determined by methods well known in the art. The term "differentially expressed" or "differential expression" refers to an increase or decrease in the measurable expression level of a given nucleic acid. As used herein, "differentially expressed" or "differential expression" means the difference in the level of expression of a nucleic acid is at least 1.4-fold or more in two samples used for comparison, both of which are compared to the same normal standard sample. "Differentially expressed" or "differential expression" according to the invention also means a 1.4-fold, or more, up to and including 2-fold, 5-fold, 10-fold, 20-fold, 50-fold or more difference in the level of expression of a nucleic acid in two samples used for comparison. A nucleic acid is also said to be "differentially expressed" in two samples if one of the two samples contains no detectable expression of a given nucleic acid, provided that the detectably expressed nucleic acid is expressed at +/− at least 1.4 fold. Differential expression of a nucleic acid sequence is "inhibited" the difference in the level of expression of the nucleic acid in two or more samples used for comparison is altered such that it is no longer at least a 1.4 fold difference. Absolute quantification of the level of expression of a nucleic acid may be accomplished by including a known concentration(s) of one or more control nucleic acid species, generating a standard curve based on the amount of the control nucleic acid and extrapolating the expression level of the "unknown" nucleic acid species from the hybridization intensities of the unknown with respect to the standard curve.

As used herein, the term "nucleic acid" refers to polynucleotides such as deoxyribonucleic acid (DNA) and, where appropriate, ribonucleic acid (RNA). The term should also be understood to include, as equivalents, analogs of either RNA or DNA made from nucleotide analogs and, as applicable to the embodiment being described, single-stranded (sense or antisense) and double-stranded polynucleotides. Chromosomes, cDNAs, mRNAs, rRNAs, and ESTs are representative examples of molecules that may be referred to as nucleic acids.

The term "oligonucleotide" as used herein refers to a nucleic acid molecule comprising, for example, from about 10 to about 1000 nucleotides. Oligonucleotides for use in the present invention are preferably from about 15 to about 150 nucleotides, more preferably from about 150 to about 1000 in length. The oligonucleotide may be a naturally occurring oligonucleotide or a synthetic oligonucleotide. Oligonucleotides may be prepared by the phosphoramidite method (Beaucage and Carruthers, Tetrahedron Lett. 22:1859-62, 1981), or by the triester method (Matteucci, et al., J. Am. Chem. Soc. 103:3185, 1981), or by other chemical methods known in the art.

The term "patient" or "subject" as used herein includes mammals (e.g., humans and animals).

As used herein, a nucleic acid or other molecule attached to an array is referred to as a "probe" or "capture probe." When an array contains several probes corresponding to one gene, these probes are referred to as a "gene-probe set." A gene-probe set may consist of, for example, about 2 to about 20 probes, preferably from about 2 to about 10 probes, and most preferably about 5 probes.

The "profile" of a cell's biological state refers to the levels of various constituents of a cell that are known to change in response to drug treatments and other perturbations of the biological state of the cell. Constituents of a cell include, for example, levels of RNA, levels of protein abundances, or protein activity levels.

The term "protein" is used interchangeably herein with the terms "peptide" and "polypeptide."

An expression profile in one cell is "similar" to an expression profile in another cell when the level of expression of the genes in the two profiles are sufficiently similar that the similarity is indicative of a common characteristic, for example, the same type of cell. Accordingly, the expression profiles of a first cell and a second cell are similar when at least 75% of the genes that are expressed in the first cell are expressed in the second cell at a level that is within a factor of two relative to the first cell.

"Small molecule," as used herein, refers to a composition with a molecular weight of less than about 5 kD and most preferably less than about 4 kD. Small molecules can be nucleic acids, peptides, polypeptides, peptidomimetics, carbohydrates, lipids, or other organic or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

The term "specific hybridization" of a probe to a target site of a template nucleic acid refers to hybridization of the probe predominantly to the target, such that the hybridization signal can be clearly interpreted. As further described herein, such conditions resulting in specific hybridization vary depending on the length of the region of homology, the GC content of the region, and the melting temperature ("Tm") of the hybrid. Thus, hybridization conditions may vary in salt content, acidity, and temperature of the hybridization solution and the washes.

A "variant" of polypeptide refers to a polypeptide having an amino acid sequence in which one or more amino acid residues is altered. The variant may have "conservative" changes, wherein a substituted amino acid has similar structural or chemical properties (e.g., replacement of leucine with isoleucine). A variant may also have "nonconservative" changes (e.g., replacement of glycine with tryptophan). Analogous minor variations may include amino acid deletions or insertions, or both. Guidance in determining which amino acid residues may be substituted, inserted, or deleted without abolishing biological or immunological activity may be identified using computer programs well known in the art, for example, LASERGENE software (DNASTAR).

The term "variant," when used in the context of a polynucleotide sequence, may encompass a polynucleotide sequence related to that of a particular gene or the coding sequence thereof. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

An aspect of the invention is directed to the identification of agents capable of modulating the differentiation and proliferation of cells characterized by aberrant proliferation. More specifically, the invention relates to methods of screening candidate compounds or substances for their ability to regulate the differential expression of nucleic acid sequences. That is, if a nucleic acid sequence is overexpressed in cancer cells, then the candidate compounds are screened for their ability to decrease expression, and if a nucleic acid sequence is under-expressed in cancer cells, then a test compound is screened for its ability to increase expression. In addition, the invention relates to screening assays to identify test compounds or substances which modulate the activity of one or more polypeptides which are encoded by the differentially expressed sequences described herein. In this regard, the invention provides assays for determining compounds that modulate the expression of marker nucleic acids and/or alter the bioactivity of the encoded polypeptide.

Screening for Modulation of Differential Expression

Drug screening is performed by adding a test compound (e.g., sorafenib) to a sample of cells, and monitoring the effect. A parallel sample which does not receive the test compound is also monitored as a control. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, and the ability of the cells to interact with other cells or compounds. Differences between treated and untreated cells indicates effects attributable to the test compound.

Desirable effects of a test compound include an effect on any phenotype that was conferred by the cancer-associated marker nucleic acid sequence. Examples include a test compound that limits the overabundance of mRNA, limits production of the encoded protein, or limits the functional effect of the protein. The effect of the test compound would be apparent when comparing results between treated and untreated cells.

The invention thus, also encompasses methods of screening for agents (e.g., sorafenib which inhibit or enhance the expression of the nucleic acid markers in vitro, comprising exposing a cell or tissue in which the marker nucleic acid mRNA or protein (e.g., HER-2 or VEGF) is detectable in cultured cells to an agent in order to determine whether the agent is capable of inhibiting or enhancing production of the mRNA; and determining the level of mRNA in the exposed cells or tissue, wherein a decrease in the level of the mRNA after exposure of the cell line to the agent is indicative of inhibition of the marker nucleic acid mRNA production and an increase in mRNA levels is indicative of enhancement of maker mRNA production.

Alternatively, the screening method may include in vitro screening of a cell or tissue in which marker protein is detectable in cultured cells to an agent suspected of inhibiting or enhancing production of the marker protein; and determining the level of the marker protein in the cells or tissue, wherein a decrease in the level of marker protein after exposure of the cells or tissue to the agent is indicative of inhibition of marker protein production and an increase on the level of marker protein is indicative of enhancement of marker protein production.

The invention also encompasses in vivo methods of screening for agents which inhibit or enhance expression of the marker nucleic acids, comprising exposing a subject having tumor cells in which marker mRNA or protein is detectable to an agent suspected of inhibiting or enhancing production of marker mRNA or protein; and determining the level of marker mRNA or protein in tumor cells of the exposed mammal. A decrease in the level of marker mRNA or protein after exposure of the subject to the agent is indicative of inhibition of marker nucleic acid expression and an increase in the level of marker mRNA or protein is indicative of enhancement of marker nucleic acid expression.

Accordingly, the invention provides a method comprising incubating a cell expressing the marker nucleic acids with a test compound and measuring the mRNA or protein level. The invention further provides a method for quantitatively determining the level of expression of the marker nucleic acids in a cell population, and a method for determining whether an agent is capable of increasing or decreasing the level of expression of the marker nucleic acids in a cell population. The method for determining whether an agent is capable of increasing or decreasing the level of expression of the marker nucleic acids in a cell population comprises the steps of (a) preparing cell extracts from control and agent-treated cell populations, (b) isolating the marker polypeptides from the cell extracts, and (c) quantifying (e.g., in parallel) the amount of an immunocomplex formed between the marker polypeptide and an antibody specific to said polypeptide. The marker polypeptides of this invention may also be quantified by assaying for its bioactivity. Agents that induce an increase in the marker nucleic acid expression may be identified by their ability to increase the amount of immunocomplex formed in the treated cell as compared with the amount of the immunocomplex formed in the control cell. In a similar manner, agents that decrease expression of the marker nucleic acid may be identified by their ability to decrease the amount of the immunocomplex formed in the treated cell extract as compared to the control cell.

The present invention provides isolated nucleic acid sequences which are differentially regulated in cancer, and a method for identifying such sequences. The present invention provides a method for identifying a nucleotide sequence which is differentially regulated in a subject with cancer, comprising: hybridizing a nucleic acid sample corresponding to RNA obtained from the subject to a nucleic acid sample comprising one or more nucleic acid molecules of known identity; and measuring the hybridization of the nucleic acid sample to the one or more nucleic acid molecules of known identity, wherein a two-fold difference in the hybridization of the nucleic acid sample to the one or mole nucleic acid molecules of known identity relative to a nucleic acid sample obtained from a subject without cancel is indicative of the differential expression of the nucleotide sequence in a subject with cancel.

Generally, the present invention provides a method for identifying nucleic acid sequences which are differentially regulated in a subject with cancer comprising isolating messenger RNA from a subject, generating cRNA from the mRNA sample, hybridizing the cRNA to a microarray comprising a plurality of nucleic acid molecules stably associated with discrete locations on the array, and identifying patterns of hybridization of the cRNA to the array. According to the present invention, a nucleic acid molecule which hybridizes to a given location on the array is said to be differentially regulated if the hybridization signal is at least two-fold higher or lower than the hybridization signal at the same location on an identical array hybridized with a nucleic acid sample obtained from a subject that does not have cancer.

Microarrays for Determining the Level of Expression of Genes

Determining gene expression levels may be accomplished utilizing microarrays. Generally, the following steps may be involved: (a) obtaining an mRNA sample from a subject and preparing labeled nucleic acids therefrom (the "target nucleic acids" or "targets"); (b) contacting the target nucleic acids with an array under conditions sufficient for the target nucleic acids to bind to the corresponding probes on the array, for example, by hybridization or specific binding; (c) optional removal of unbound targets from the array; (d) detecting the bound targets, and (e) analyzing the results, for example, using computer based analysis methods. As used herein, "nucleic acid probes" or "probes" are nucleic acids attached to the array, whereas "target nucleic acids" are nucleic acids that are hybridized to the array.

Nucleic acid specimens may be obtained from a subject to be tested using either "invasive" or "non-invasive" sampling means. A sampling means is said to be "invasive" if it involves the collection of nucleic acids from within the skin or organs of an animal (including murine, human, ovine, equine, bovine, porcine, canine, or feline animal). Examples of invasive methods include, for example, blood collection, semen collection, needle biopsy, pleural aspiration, umbilical cord biopsy. Examples of such methods are discussed by Kim, et al., (J. Virol. 66:3879-3882, 1992); Biswas, et al., (Ann. NY Acad. Sci. 590:582-583, 1990); and Biswas, et al., (J. Clin. Microbiol. 29:2228-2233, 1991).

In contrast, a "non-invasive" sampling means is one in which the nucleic acid molecules are recovered from an internal or external surface of the animal. Examples of such "non-invasive" sampling means include, for example, "swabbing," collection of tears, saliva, urine, fecal material, sweat or perspiration, hair.

In one embodiment of the present invention, one or more cells from the subject to be tested are obtained and RNA is isolated from the cells. In a preferred embodiment, a sample of peripheral blood leukocytes (PBLs) cells is obtained from the subject. It is also possible to obtain a cell sample from a subject, and then to enrich the sample for a desired cell type. For example, cells may be isolated from other cells using a variety of techniques, such as isolation with an antibody binding to an epitope on the cell surface of the desired cell type. Where the desired cells are in a solid tissue, particular cells may be dissected, for example, by microdissection or by laser capture microdissection (LCM) (see, e.g., Bonner, et al., Science 278:1481, 1997; Emmert-Buck, et al., Science 274: 998, 1996; Fend, et al., Am. J. Path. 154:61,1999; and Murakami, et al., Kidney Int. 58:1346, 2000).

RNA may be extracted from tissue or cell samples by a variety of methods, for example, guanidium thiocyanate lysis followed by CsCl centrifugation (Chirgwin, et al., Biochemistry 18:5294-5299, 1979). RNA from single cells may be obtained as described in methods for preparing cDNA libraries from single cells (see, e.g., Dulac, Curr. Top. Dev. Biol. 36:245, 1998; Jena, et al., J. Immunol. Methods 190:199, 1996).

The RNA sample can be further enriched for a particular species. In one embodiment, for example, poly(A)+ RNA may be isolated from an RNA sample. In another embodiment, the RNA population may be enriched for sequences of interest by primer-specific cDNA synthesis, or multiple rounds of linear amplification based on cDNA synthesis and template-directed in vitro transcription (see, e.g., Wang, et al., Proc. Natl. Acad. Sci. USA 86:9717, 1989; Dulac, et al., supra; Jena, et al., supra). In addition, the population of RNA, enriched or not in particular species or sequences, may be further amplified by a variety of amplification methods including, for example, PCR; ligase chain reaction (LCR) (see, e.g., Wu and Wallace, Genomics 4:560, 1989; Landegren, et al., Science 241:1077, 1988); self-sustained sequence replication (SSR) (see, e.g., Guatelli, et al., Proc. Natl. Acad. Sci. USA 87:1874, 1990); nucleic acid based sequence amplification (NASBA) and transcription amplification (see, e.g., Kwoh, et al., Proc. Natl. Acad. Sci. USA 86:1173, 1989). Methods for PCR technology are well known in the art (see, e.g., PCR Technology: Principles and Applications for DNA Amplification (ed. H. A. Erlich, Freeman Press, N.Y., N.Y., 1992); PCR Protocols: A Guide to Methods and Applications (eds. Innis, et al., Academic Press, San Diego, Calif., 1990); Mattila, et al., Nucleic Acids Res. 19:4967, 1991; Eckert, et al., PCR Methods and Applications 1:17, 1991; PCR (eds. McPherson et al., IRL Press, Oxford); and U.S. Pat. No. 4,683,202). Methods of amplification are described, for example, by Ohyama, et al., (BioTechniques 29:530, 2000); Luo, et al., (Nat. Med. 5:117, 1999); Hegde, et al., (BioTechniques 29:548, 2000); Kacharmina, et al., (Meth. Enzymol. 303:3, 1999); Livesey, et al., Curr. Biol. 10:301, 2000); Spirin, et al., (Invest. Ophtalmol. Vis. Sci. 40:3108, 1999); and Sakai, et al., (Anal. Biochem. 287:32, 2000). RNA amplification and cDNA synthesis may also be conducted in cells in situ (see, e.g., Eberwine, et al. Proc. Natl. Acad. Sci. USA 89:3010, 1992).

The nucleic acid molecules may be labeled to permit detection of hybridization of the nucleic acid molecules to a microarray. That is, the probe may comprise a member of a signal producing system and thus, is detectable, either directly or through combined action with one or more additional members of a signal producing system. For example, the nucleic acids may be labeled with a fluorescently labeled dNTP (see, e.g., Kricka, 1992, Nonisotopic DNA Probe Techniques, Academic Press San Diego, Calif.), biotinylated dNTPs or rNTP followed by addition of labeled streptavidin, chemiluminescent labels, or isotopes. Another example of labels include "molecular beacons" as described in Tyagi and Kramer (Nature Biotech. 14:303, 1996). Hybridization may be also be determined, for example, by plasmon resonance (see, e.g., Thiel, et al. Anal. Chem. 69:4948, 1997).

In one embodiment, a plurality (e.g., 2, 3, 4, 5, or more) of sets of target nucleic acids are labeled and used in one hybridization reaction ("multiplex" analysis). For example, one set of nucleic acids may correspond to RNA from one cell and another set of nucleic acids may correspond to RNA from another cell. The plurality of sets of nucleic acids may be labeled with different labels, for example, different fluorescent labels (e.g., fluorescein and rhodamine) which have distinct emission spectra so that they can be distinguished. The sets may then be mixed and hybridized simultaneously to one microarray (see, e.g., Shena, et al., Science 270:467-470, 1995).

Microarrays for use according to the invention include one or more probes of genes characteristic of small molecule efficacy. In a preferred embodiment, the microarray comprises probes corresponding to one or more of genes selected from the group consisting of genes which are up-regulated in cancer and genes which are down-regulated in cancer. The microarray may comprise probes corresponding to at least 10, preferably at least 20, at least 50, at least 100 or at least 1000 genes characteristic of small molecule efficacy.

There may be one or more than one probe corresponding to each gene on a microarray. For example, a microarray may contain from 2 to 20 probes corresponding to one gene and preferably about 5 to 10. The probes may correspond to the full-length RNA sequence or complement thereof of genes characteristic of small molecule efficacy, or the probe may correspond to a portion thereof, which portion is of sufficient length to permit specific hybridization. Such probes may comprise from about 50 nucleotides to about 100, 200, 500, or 1000 nucleotides or more than 1000 nucleotides. As further described herein, microarrays may contain oligonucleotide probes, consisting of about 10 to 50 nucleotides, preferably about 15 to 30 nucleotides and more preferably about 20-25 nucleotides. The probes are preferably single-stranded and will have sufficient complementarity to its target to provide for the desired level of sequence specific hybridization.

Typically, the arrays used in the present invention will have a site density of greater than 100 different probes per $cm^2$. Preferably, the arrays will have a site density of greater than $500/cm^2$, more preferably greater than about $1000/cm^2$, and most preferably, greater than about $10,000/cm^2$. Preferably, the arrays will have more than 100 different probes on a single substrate, more preferably greater than about 1000 different probes, still more preferably, greater than about 10,000 different probes and most preferably, greater than 100,000 different probes on a single substrate.

A number of different microarray configurations and methods for their production are known to those of skill in the art and are disclosed in U.S. Pat. Nos.: 5,242,974; 5,384,261; 5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,700,637; 5,744,305; 5,770,456; 5,770,722; 5,837,832; 5,856,101; 5,874,219; 5,885,837; 5,919,523; 6,022,963; 6,077,674; and 6,156,501; Shena, et al., Tibtech 16:301, 1998; Duggan, et al., Nat. Genet. 21:10, 1999; Bowtell, et al., Nat. Genet. 21:25, 1999; Lipshutz, et al., 21 Nature Genet. 20-24, 1999; Blanchard, et al., 11 Biosensors and Bioelectronics, 687-90, 1996; Maskos, et al., 21 Nucleic Acids Res. 4663-69, 1993; Hughes, et al., Nat. Biotechnol. (2001) 19:342; the disclosures of which are herein incorporated by reference. Patents describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; and 5,874,219; the disclosures of which are herein incorporated by reference.

Arrays preferably include control and reference nucleic acids. Control nucleic acids include, for example, prokaryotic genes such as bioB, bioC and bioD, cre from PI bacteriophage or polyA controls, such as dap, lys, phe, thr, and trp. Reference nucleic acids allow the normalization of results from one experiment to another and the comparison of multiple experiments on a quantitative level. Exemplary reference nucleic acids include housekeeping genes of known expression levels, for example, GAPDH, hexokinase, and actin.

In one embodiment, an array of oligonucleotides may be synthesized on a solid support. Exemplary solid supports include glass, plastics, polymers, metals, metalloids, ceramics, organics, etc. Using chip masking technologies and photoprotective chemistry, it is possible to generate ordered arrays of nucleic acid probes. These arrays, which are known, for example, as "DNA chips" or very large scale immobilized polymer arrays ("VLSIPS™" arrays), may include millions of defined probe regions on a substrate having an area of about 1 $cm^2$ to several $cm^2$, thereby incorporating from a few to millions of probes (see, e.g., U.S. Pat. No. 5,631,734).

To compare expression levels, labeled nucleic acids may be contacted with the array under conditions sufficient for binding between the target nucleic acid and the probe on the array. In a preferred embodiment, the hybridization conditions may be selected to provide for the desired level of hybridization specificity; that is, conditions sufficient for hybridization to occur between the labeled nucleic acids and probes on the microarray.

Hybridization may be carried out in conditions permitting essentially specific hybridization. The length and GC content of the nucleic acid will determine the thermal melting point and thus, the hybridization conditions necessary for obtaining specific hybridization of the probe to the target nucleic acid. These factors are well known to a person of skill in the art, and may also be tested in assays. An extensive guide to nucleic acid hybridization may be found in Tijssen, et al. (Laboratory Techniques in Biochemistry and Molecular Biology, Vol. 24: Hybridization With Nucleic Acid Probes, P. Tijssen, ed. Elsevier, N.Y., (1993)).

The methods described above result in the production of hybridization patterns of labeled target nucleic acids on the array surface. The resultant hybridization patterns of labeled nucleic acids may be visualized or detected in a variety of ways, with the particular manner of detection selected based on the particular label of the target nucleic acid. Representative detection means include scintillation counting, autoradiography, fluorescence measurement, colorimetric measurement, light emission measurement, light scattering, and the like.

One such method of detection utilizes an array scanner that is commercially available (Affymetrix, Santa Clara, Calif.), for example, the 417™ Arrayer, the 418™ Array Scanner, or the Agilent GeneArray™ Scanner. This scanner is controlled from a system computer with an interface and easy-to-use software tools. The output may be directly imported into or directly read by a variety of software applications. Preferred scanning devices are described in, for example, U.S. Pat. Nos. 5,143,854 and 5,424,186.

For fluorescent labeled probes, the fluorescence emissions at each site of a transcript array may be, preferably, detected by scanning confocal laser microscopy. Alternatively, a laser may be used that allows simultaneous specimen illumination at wavelengths specific to the two fluorophores and emissions from the two fluorophores may be analyzed simultaneously (see, e.g., Shalon, et al., Genome Res. 6:639-645, 1996). In a preferred embodiment, the arrays may be scanned with a laser fluorescent scanner with a computer controlled X-Y stage and a microscope objective. Fluorescence laser scanning devices are described in Shalon, et al., supra.

Various algorithms are available for analyzing gene expression data, for example, the type of comparisons to perform. In certain embodiments, it is desirable to group genes that are co-regulated. This allows for the comparison of large numbers of profiles. A preferred embodiment for identifying such groups of genes involves clustering algorithms (for reviews of clustering algorithms, see, e.g., Fukunaga, 1990, Statistical Pattern Recognition, 2nd Ed., Academic Press, San Diego; Everitt, 1974, Cluster Analysis, London: Heinemann Educ. Books; Hartigan, 1975, Clustering Algorithms, New York: Wiley; Sneath and Sokal, 1973, Numerical Taxonomy, Freeman; Anderberg, 1973, Cluster Analysis for Applications, Academic Press: New York).

Biomarker Discovery

Expression patterns may be used to derive a panel of biomarkers that can be used to predict the efficacy of drug treatment in the patients. The biomarkers may consist of gene expression levels from microarray experiments on RNA isolated from biological samples, RNA isolated from frozen samples of tumor biopsies, or mass spectrometry-derived protein masses in the serum.

Although the precise mechanism for data analysis will depend upon the exact nature of the data, a typical procedure for developing a panel of biomarkers is as follows. The data (gene expression levels or mass spectra) are collected for each patient prior to treatment. As the study progresses, the patients are classified according to their response to the drug treatment; either as efficacious or non-efficacious. Multiple levels of efficacy can be accommodated in a data model, but a binary comparison is considered optimal, particularly if the patient population is less than several hundred. Assuming adequate numbers of patients in each class, the protein and/or gene expression data may be analyzed by a number of techniques known in the art. Many of the techniques are derived from traditional statistics as well from the field of machine learning. These techniques serve two purposes:

1. Reduce the dimensionality of data—In the case of mass spectra or gene expression microarrays, data is reduced from many thousands of individual data points to bout three to ten. The reduction is based upon the predictive power of the data points when taken as a set.

2. Training—These three to ten data points are then used to train multiple machine learning algorithms which then "learn" to recognize, in this case, patterns of protein masses or gene expression which distinguish efficacious drug treatment from non-efficacious. All patient samples can be used to train the algorithms.

The resulting, trained, algorithms are then tested in order to measure their predictive power. Typically, when less than many hundreds of training examples are available, some for m of cross-validation is performed. To illustrate, consider a ten-fold cross validation. In this case, patient samples are randomly assigned to one of ten bins. In the first round of validation the samples in nine of the bins are used for training and the remaining samples in the tenth bin are used to test the algorithm. This is repeated an additional nine times, each time leaving out the samples in a different bin for testing. The results (correct predictions and errors) from all ten rounds are combined and the predictive power is then assessed. Different algorithms, as well as different panels, may be compared in this way for this study. The "best" algorithm/panel combination will then be selected. This "smart" algorithm may then be used in future studies to select the patients that are most likely to respond to treatment.

Many algorithms benefit from additional information taken for the patients. For example, gender or age could be used to improve predictive power. Also, data transformations such as normalization and smoothing may be used to reduce noise. Because of this, a large number of algorithms may be trained using many different parameters in order to optimize the outcome. If j predictive patterns exist in the data, it is likely that an optimal, or near-optimal, "smart" algorithm can be developed. If more patient samples become available, the algorithm can be retrained to take advantage of the new data.

As an example using mass spectrometry, plasma (1 µl) may be applied to a hydrophobic SELDI-target, washed extensively in water, and analyzed by the SELDI-T of mass spectrometer. This may be repeated on 100 or more patient samples. The protein profiles resulting from the intensities of some 16,000 m/z values in each sample would be statistically analyzed in order to identify sets of specific m/z values that are predictive of drug efficacy. Identical experiments using other SELDI-targets, such as ion-exchange or IMAC surfaces, could also be conducted. These will capture different subsets of the proteins present in plasma. Furthermore, the plasma may be denatured and prefractionated prior to application onto the SELDI target.

Diagnostic & Prognostic Assays

The biomarkers of the present invention can be utilized to determine and tailor treatment therapy in various classes of patients having cancer, including patients who have not received treatment, as well as patients already undergoing therapy, such as chemotherapy and radiation. In addition, the biomarkers can be used to monitor patients under active treatment to determine therapeutic efficacy and to indicate whether additional chemotherapeutic agents are needed, or whether the therapeutic course needs to be modified.

Especially useful as a prognostic marker is soluble HER-2 and/or soluble VEGF polypeptide which, when higher than baseline levels are measured in the blood of subjects, a shorter time to progression of the cancer (e.g., a breast cancer) is observed, especially in those patients who have received anti-HER-2 therapy. Thus, elevated levels of these markers in patients are indicative of poor prognosis, and suggest the use of additional therapy, e.g., sorafenib or other chemotherapeutic agents.

Another useful prognostic marker is soluble EGFR polypeptide which, when higher than baseline levels are measured in the blood of subjects, a longer time to death as a result of the cancer (e.g., a breast cancer) is observed, especially in those patients who have received anti-HER-2 therapy. Thus, soluble EGFR indicates a more positive prognosis, and patients with elevated levels of it can benefit from sorafenib (alone or in combination with another chemotherapeutic agent, such as anti-HER-2).

Examples of useful chemotherapeutic agents include, but are not limited to, e.g., Examples of chemotherapeutic agents include, but are not limited to, e.g., alkylating agents (e.g., cyclophosphamide, ifosfamide, melphalan, chlorambucil, aziridines, epoxides, alkyl sulfonates), cisplatin and its analogues (e.g., carboplatin, oxaliplatin), antimetabolitites (e.g., methotrexate, 5-fluorouracil, capecitabine, cytarabine, gemcitabine, fludarabine), toposiomerase interactive agents (e.g., camptothecin, irinotecan, topotecan, etoposide, teniposide, doxorubicin, daunorubicin), antimicrotubule agents (e.g., vinca alkaloids, such as vincristine, vinblastine, and vinorelbine; taxanes, such as paclitaxel and docetaxel), inteleukin-2, histone deacetylase inhibitors, monoclonal antibodies, estrogen modulators (e.g., tamoxifen, toremifene, raloxifene), megestrol, aromatase inhibitors (e.g., letrozole, anastrozole, exemestane, octreotide), octreotide, anti-androgens (e.g., flutamide, casodex), interferons (e.g., interferon-alpha, including subtypes thereof, such as interferon-alpha-2a), etc. See, e.g. Cancer: Principles and Practice of Oncology, 7th Edtion, Devita et al, Lippincott Williams & Wilkins, 2005, Chapters 15, 16, 17, and 63.

The present invention provides methods for determining whether a subject is at risk for developing a disease or condition characterized by unwanted cell proliferation by detecting biomarkers (e.g., HER-2, EGFR, VEGF, u-PA, p-PAI-1, and soluble forms thereof), that is, nucleic acids and/or polypeptide markers for cancer.

In clinical applications, human tissue samples may be screened for the presence and/or absence of biomarkers identified herein. Such samples could consist of needle biopsy cores, surgical resection samples, lymph node tissue, or serum. For example, these methods include obtaining a biopsy, which is optionally fractionated by cryostat sectioning to enrich tumor cells to about 80% of the total cell population. In certain embodiments, nucleic acids extracted from these samples may be amplified using techniques well known in the art. The levels of selected markers detected would be compared with statistically valid groups of metastatic, non-metastatic malignant, benign, or normal tissue samples.

In one embodiment, the diagnostic method comprises determining whether a subject has an abnormal mRNA and/or protein level of the biomarkers (e.g., HER-2, EGFR, VEGF, u-PA (urokinase-plasminogen activator), p-PAI-1, and soluble forms thereof), such as by Northern blot analysis, reverse transcription-polymerase chain reaction (RT-PCR), in situ hybridization, immunoprecipitation, Western blot hybridization, or immunohistochemistry. According to the method, cells may be obtained from a subject and the levels of the biomarkers, protein, or mRNA level, are determined and compared to the level of these markers in a healthy subject. An abnormal level of the biomarker polypeptide or mRNA levels is likely to be indicative of cancer.

Accordingly, in one aspect, the invention provides probes and primers that are specific to the unique nucleic acid markers disclosed herein. Accordingly, the nucleic acid probes comprise a nucleotide sequence at least 10 nucleotides in length, preferably at least 15 nucleotides, more preferably, 25 nucleotides, and most preferably at least 40 nucleotides, and up to all or nearly all of the coding sequence which is complementary to a portion of the coding sequence of a marker nucleic acid sequence.

In one embodiment, the method comprises using a nucleic acid probe to determine the presence of cancerous cells in a tissue from a patient. Specifically, the method comprises:
1. providing a nucleic acid probe comprising a nucleotide sequence at least 10 nucleotides in length, preferably at least 15 nucleotides, more preferably, 25 nucleotides, and most preferably at least 40 nucleotides, and up to all or nearly all of the coding sequence which is complementary to a portion of the coding- sequence of a nucleic acid sequence and is differentially expressed in tumors cells;
2. obtaining a tissue sample from a patient potentially comprising, cancerous cells;
3. providing a second tissue sample containing cells substantially all of which are non-cancerous;
4. contacting the nucleic acid probe under stringent conditions with RNA of each of said first and second tissue samples (e.g., in a Northern blot or in situ hybridization assay); and
5. comparing (a) the amount of hybridization of the probe with RNA of the first tissue sample, with (b) the amount of hybridization of the probe with RNA of the second tissue sample; wherein a statistically significant difference in the amount of hybridization with the RNA of the first tissue sample as compared to the amount of hybridization with the RNA of the second tissue sample is indicative of the presence of cancerous cells in the first tissue sample.

In one aspect, the method comprises in situ hybridization with a probe derived from a given marker nucleic acid sequence (e.g., HER-2, EGFR, VEGF, u-PA, p-PAI-1, and soluble forms thereof). The method comprises contacting the labeled hybridization probe with a sample of a given type of tissue potentially containing cancerous or pre-cancerous cells as well as normal cells, and determining whether the probe labels some cells of the given tissue type to a degree significantly different (e.g., by at least a factor of two, or at least a factor of five, or at least a factor of twenty, or at least a factor of fifty) than the degree to which it labels other cells of the same tissue type.

Also within the invention is a method of determining the phenotype of a test cell from a given human tissue, for example, whether the cell is (a) normal, or (b) cancerous or precancerous, by contacting the mRNA of a test cell with a nucleic acid probe at least 12 nucleotides in length, preferably at least 15 nucleotides, more preferably at least 25 nucleotides, and most preferably at least 40 nucleotides, and up to all or nearly all of a sequence which is complementary to a portion of the coding sequence of a nucleic acid sequence, and which is differentially expressed in tumor cells as compared to normal cells of the given tissue type; and determining the approximate amount of hybridization of the probe to the mRNA, an amount of hybridization either more or less than that seen with the mRNA of a normal cell of that tissue type being indicative that the test cell is cancerous or pre-cancerous.

Alternatively, the above diagnostic assays may be carried out using antibodies to detect the protein product encoded by the marker nucleic acid sequence (e.g., HER-2, EGFR, VEGF, u-PA, p-PAI-1, and soluble forms thereof). Accordingly, in one embodiment, the assay would include contacting the proteins of the test cell with an antibody specific for the gene product of a nucleic acid, the marker nucleic acid being one which is expressed at a given control level in normal cells of the same tissue type as the test cell, and determining the approximate amount of immunocomplex formation by the antibody and the proteins of the test cell, wherein a statistically significant difference in the amount of the immunocomplex formed with the proteins of a test cell as compared to a normal cell of the same tissue type is an indication that the test cell is cancerous or pre-cancerous. Preferably, the antibody is specific for HER-2, EGFR, VEGF, u-PA, p-PAI-1, and soluble forms thereof.

The method for producing polyclonal and/or monoclonal antibodies which specifically bind to polypeptides useful in the present invention is known to those of skill in the art and may be found in, for example, Dymecki, et al., (J. Biol. Chem. 267:4815, 1992); Boersina & Van Leeuwen, (J. Neuosci. Methods 51:317, 1994); Green, et al., (Cell 28:477, 1982); and Arnheiter, et al., (Nature 294:278, 1981).

Another such method includes the steps of: providing an antibody specific for the gene product of a marker nucleic acid sequence, the gene product being present in cancerous tissue of a given tissue type at a level more or less than the level of the gene product in non-cancerous tissue of the same tissue type; obtaining from a patient a first sample of tissue of the given tissue type, which sample potentially includes cancerous cells; providing a second sample of tissue of the same tissue type (which may be from the same patient or from a normal control, e.g. another individual or cultured cells), this second sample containing normal cells and essentially no cancerous cells; contacting the antibody with protein (which may be partially purified, in lysed but unfractionated cells, or in siti) of the first and second samples under conditions permitting immunocomplex formation between the antibody and the marker nucleic acid sequence product present in the samples; and comparing (a) the amount of immunocomplex formation in the first sample, with (b) the amount of immunocomplex formation in the second sample, wherein a statistically significant difference in the amount of immunocomplex formation in the first sample less as compared to the amount of immunocomplex formation in the second sample is indicative of the presence of cancerous cells in the first sample of tissue.

The subject invention further provides a method of determining whether a cell sample obtained from a subject possesses an abnormal amount of marker polypeptide which comprises (a) obtaining a cell sample from the subject, (b) quantitatively determining the amount of the marker polypeptide in the sample so obtained, and (c) comparing the amount of the marker polypeptide so determined with a known standard, so as to thereby determine whether the cell sample obtained from the subject possesses an abnormal amount of the marker polypeptide. Such marker polypeptides may be detected by immunohistochemical assays, dot-blot assays, ELISA, and the like.

Immunoassays are commonly used to quantitate the levels of proteins in cell samples, and many other immunoassay techniques are known in the art. The invention is not limited to a particular assay procedure, and therefore, is intended to include both homogeneous and heterogeneous procedures. Exemplary immunoassays which may be conducted according to the invention include fluorescence polarization immunoassay (FPIA), fluorescence immunoassays (FIA), enzyme immunoassay (EIA), nephelometric inhibition immunoassay (NIA), enzyme-linked immunosorbent assay (ELISA), and radioimmunoassay (RIA). An indicator moiety, or label group, may be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In another embodiment, the level of the encoded product, or alternatively the level of the polypeptide, in a biological fluid (e.g., blood or urine) of a patient may be determined as a way of monitoring the level of expression of the marker nucleic acid sequence in cells of that patient. Such a method would include the steps of obtaining a sample of a biological fluid from the patient, contacting the sample (or proteins from the sample) with an antibody specific for an encoded marker polypeptide, and determining the amount of immune complex formation by the antibody, with the amount of immune complex formation being indicative of the level of the marker encoded product in the sample. This determination is particularly instructive when compared to the amount of immune complex formation by the same antibody in a control sample taken from a normal individual or in one or more samples previously or subsequently obtained from the same person.

In another embodiment, the method may be used to determine the amount of marker polypeptide present in a cell, which in turn may be correlated with progression of a hyperproliferative disorder. The level of the marker polypeptide may be used predictively to evaluate whether a sample of cells contains cells which are, or are predisposed towards becoming, transformed cells. Moreover, the subject method may be used to assess the phenotype of cells which are known to be transformed, the phenotyping results being useful in planning a particular therapeutic regimen. For example, very high levels of the marker polypeptide in sample cells is a powerful diagnostic and prognostic marker for a cancer. The observation of marker potypeptide levels may be utilized in decisions regarding, for example, the use of more aggressive therapies.

As set out above, one aspect of the present invention relates to diagnostic assays for determining, in the context of cells isolated from a patient, if the level of a marker polypeptide is significantly reduced in the sample cells. The term "significantly reduced" refers to a cell phenotype wherein the cell possesses a reduced cellular amount of the marker polypeptide relative to a normal cell of similar tissue origin. For example, a cell may have less than about 50%, 25%, 10%, or 5% of the marker polypeptide compared to that of a normal control cell. In particular, the assay evaluates the level of marker polypeptide in the test cells, and, preferably, compares the measured level with marker polypeptide detected in at least one control cell, for example, a normal cell and/or a transformed cell of known phenotype.

Of particular importance to the subject invention is the ability to quantitate the level of marker polypeptide as determined by the number of cells associated with a normal or abnormal marker polypeptide level. The number of cells with a particular marker polypeptide phenotype may then be correlated with patient prognosis. In one embodiment of the invention, the marker polypeptide phenotype of a lesion is determined as a percentage of cells in a biopsy which are found to have abnormally high/low levels of the marker polypeptide. Such expression may be detected by immunohistochemical assays, dot-blot assays, ELISA, and the like.

Where tissue samples are employed, immunohistochemical staining may be used to determine the number of cells having the marker polypeptide phenotype. For such staining, a multiblock of tissue may be taken from the biopsy or other tissue sample and subjected to proteolytic hydrolysis, employing such agents as protease K or pepsin. In certain embodiments, it may be desirable to isolate a nuclear fraction from the sample cells and detect the level of the marker polypeptide in the nuclear fraction.

The tissue samples are fixed by treatment with a reagent such as formal in, glutaraldehyde, methanol, or the like. The samples are then incubated with an antibody, preferably a monoclonal antibody, with binding specificity for the marker polypeptides. This antibody may be conjugated to a label for subsequent detection of binding. Samples are incubated for a time sufficient for formation of the immunocomplexes. Binding of the antibody is then detected by virtue of a label conjugated to this antibody. Where the antibody is unlabeled, a second labeled antibody may be employed, for example, which is specific for the isotype of the anti-marker polypeptide antibody. Examples of labels which may be employed include radionuclides, fluorescers, chemiluminescers, enzymes, and the like.

Where enzymes are employed, the substrate for the enzyme may be added to the samples to provide a colored or fluorescent product. Examples of suitable enzymes for use in conjugates include horseradish peroxidase, alkaline phosphatase, malate dehydrogenase, and the like. Where not commercially available, such antibody-enzyme conjugates are readily produced by techniques known to those skilled in the art.

In one embodiment, the assay is performed as a dot blot assay. The dot blot assay finds particular application where tissue samples are employed as it allows determination of the average amount of the marker polypeptide associated with a single cell by correlating the amount of marker polypeptide in a cell-free extract produced from a predetermined number of cells.

It is well established in the cancer literature that tumor cells of the same type (e.g., breast and/or colon tumor cells) may not show uniformly increased expression of individual oncogenes or uniformly decreased expression of individual tumor suppressor genes. There may also be varying levels of expression of a given marker gene even between cells of a given type of cancer, further emphasizing the need for reliance on a battery of tests rather than a single test. Accordingly, in one aspect, the invention provides for a battery of tests utilizing a number of probes of the invention, in order to improve the reliability and/or accuracy of the diagnostic test.

In one embodiment, the present invention also provides a method wherein nucleic acid probes are immobilized on a DNA chip in an organized array. Oligonucleotides may be bound to a solid support by a variety of processes, including lithography. For example, a chip may hold up to 250,000 oligonucleotides. These nucleic acid probes comprise a nucleotide sequence at least about 12 nucleotides in length, preferably at least about 15 nucleotides, more preferably at least about 25 nucleotides, and most preferably at least about 40 nucleotides, and up to all or nearly all of a sequence which is complementary to a portion of the coding sequence of a marker nucleic acid sequence and is differentially expressed in tumor cells. The present invention provides significant advantages over the available tests for various cancers, because it increases the reliability of the test by providing an array of nucleic acid markers on a single chip.

The method includes obtaining a biopsy, which is optionally fractionated by cryostat sectioning to enrich tumor cells to about 80% of the total cell population. The DNA or RNA is then extracted, amplified, and analyzed with a DNA chip to determine the presence of absence of the marker nucleic acid sequences.

In one embodiment, the nucleic acid probes are spotted onto a substrate in a two-dimensional matrix or array. Samples of nucleic acids may be labeled and then hybridized to the probes. Double-stranded nucleic acids, comprising the labeled sample nucleic acids bound to probe nucleic acids, may be detected once the unbound portion of the sample is washed away.

The probe nucleic acids may be spotted on substrates including glass, nitrocellulose, etc. The probes can be bound to the substrate by either covalent bonds or by non-specific interactions, such as hydrophobic interactions. The sample nucleic acids can be labeled using radioactive labels, fluorophores, chromophores, etc.

Techniques for constructing arrays and methods of using these arrays are described, for example, in EP No. 0 799 897; PCT No. WO 97/292 12; PCT No. WO 97127317; EP No. 0 785 280; PCT No. WO 97/02357; U.S. Pat. Nos. 5,593,839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734.

Further, arrays may be used to examine differential expression of genes and may be used to determine gene function. For example, arrays of nucleic acid sequences may be used to determine if any of the nucleic acid sequences are differentially expressed between normal cells and cancer cells. Increased expression of a particular message in a cancer cell, which is not observed in a corresponding normal cell, may indicate a cancer-specific protein.

In one embodiment, nucleic acid molecules may be used to generate microarrays on a solid surface (e.g., a membrane) such that the arrayed nucleic acid molecules may be used to determine if any of the nucleic acids are differentially expressed between normal cells or tissue and cancerous cells or tissue. In one embodiment, the nucleic acid molecules of the invention may be cDNA or may be used to generate cDNA molecules to be subsequently amplified by PCR and spotted on nylon membranes. The membranes may then be reacted with radiolabeled target nucleic acid molecules obtained from equivalent samples of cancerous and normal tissue or cells. Methods of cDNA generation and microarray preparation are known to those of skill in the art and may be found, for example, in Bertucci, et al., (Hum. Mol. Genet. 8:2129, 1999); Nguyen, et al., (Genomics 29:207, 1995); Zhao, et al., (Gene 156:207); Gress, et al., (Mammalian Genome 3:609, 1992); Zhumabayeva, et al., (Biotechniques 30:158, 2001); and Lennon, et al., (Trends Genet. 7:314, 1991).

In yet another embodiment, the invention contemplates using a panel of antibodies which are generated against the marker polypeptides of this invention. Preferably, the antibodies are generated against HER-2, EGFR, VEGF, u-PA, p-PAI-1, and soluble forms thereof. Such a panel of antibodies may be used as a reliable diagnostic probe for cancer. The assay of the present invention comprises contacting a biopsy sample containing cells, for example, lung cells, with a panel of antibodies to one or more of the encoded products to determine the presence or absence of the marker polypeptides.

The diagnostic methods of the subject invention may also be employed as follow-up to treatment, for example, quantitation of the level of marker-polypeptides may be indicative of the effectiveness of current or previously employed cancer therapies as well as the effect of these therapies upon patient prognosis.

In addition, the marker nucleic acids or marker polypeptides may be utilized as part of a diagnostic panel for initial detection, follow-up screening, detection of reoccurrence, and post-treatment monitoring for chemotherapy or surgical treatment.

Accordingly, the present invention makes available diagnostic assays and reagents for detecting gain and/or loss of marker polypeptides from a cell in order to aid in the diagnosis and phenotyping of proliferative disorders arising from, for example, tumorigenic transformation of cells.

The diagnostic assays described above may be adapted to be used as prognostic assays, as well. Such an application takes advantage of the sensitivity of the assays of the invention to events which take place at characteristic stages in the progression of a tumor. For example, a given marker gene may be up- or down-regulated at a very early stage, perhaps before the cell is irreversibly committed to developing into a malignancy, while another marker gene may be characteristically up- or down-regulated only at a much later stage. Such a method could involve the steps of contacting the mRNA of a test cell with a nucleic acid probe derived from a given marker nucleic acid which is expressed at different characteristic levels in cancerous or precancerous cells at different stages of tumor progression, and determining the approximate amount of hybridization of the probe to the mRNA of the cell, such amount being an indication of the level of expression of the gene in the cell, and thus an indication of the stage of tumor progression of the cell; alternatively, the assay may be carried out with an antibody specific for the gene product of the given marker nucleic acid, contacted with the proteins of the test cell. A battery of such tests will disclose not only the existence and location of a tumor, but also will allow the clinician to select the mode of treatment most appropriate for the tumor, and to predict the likelihood of success of that treatment.

The methods of the invention may also be used to follow the clinical course of a tumor. For example, the assay of the invention may be applied to a tissue sample from a patient; following treatment of the patient for the cancer, another tissue sample is taken and the test repeated. Successful treatment will result in either removal of all cells which demonstrate differential expression characteristic of the cancerous or precancerous cells, or a substantial increase in expression of the gene in those cells, perhaps approaching or even surpassing normal levels.

In yet another embodiment, the invention provides methods for determining whether a subject is at risk for developing a disease, such as a predisposition to develop cancer, associated with aberrant activity of a polypeptide, preferably, HER-2, EGFR, VEGF, u-PA, p-PAI-1, and soluble forms thereof, wherein the aberrant activity of the polypeptide is characterized by detecting the presence or absence of a genetic lesion characterized by at least one of (a) an alteration affecting the integrity of a gene encoding a marker polypeptides, or (b) the mis-expression of the encoding nucleic acid. To illustrate, such genetic lesions may be detected by ascertaining the existence of at least one of (i) a deletion of one or more nucleotides from the nucleic acid sequence, (ii) an addition of one or more nucleotides to the nucleic acid sequence, (iii) a substitution of one or more nucleotides of the nucleic acid sequence, (iv) a gross chromosomal rearrangement of the nucleic acid sequence, (v) a gross alteration in the level of a messenger RNA transcript of the nucleic acid sequence, (vi) aberrant modification of the nucleic acid sequence, such as of the methylation pattern of the genomic DNA, (vii) the presence of a non-wild type splicing pattern of a messenger RNA transcript of the gene, (viii) a non-wild type level of the marker polypeptide, (ix) allelic loss of the gene, and/or (x) inappropriate post-translational modification of the marker polypeptide.

The present invention provides assay techniques for detecting lesions in the encoding nucleic acid sequence. These methods include, but are not limited to, methods involving sequence analysis, Southern blot hybridization, restriction enzyme site mapping, and methods involving detection of absence of nucleotide pairing between the nucleic acid to be analyzed and a probe.

Specific diseases or disorders, for example, genetic diseases or disorders, are associated with specific allelic variants of polymorphic regions of certain genes, which do not necessarily encode a mutated protein. Thus, the presence of a specific allelic variant of a polymorphic region of a gene in a subject may render the subject susceptible to developing a specific disease or disorder. Polymorphic regions in genes, may be identified, by determining the nucleotide sequence of genes in populations of individuals. If a polymorphic region is identified, then the link with a specific disease may be determined by studying specific populations of individuals, for example, individuals which developed a specific disease, such as cancer. A polymorphic region may be located in any region of a gene, for example, exons, in coding or non-coding regions of exons, introns, and promoter region.

In an exemplary embodiment, there is provided a nucleic acid composition comprising a nucleic acid probe including a region of nucleotide sequence which is capable of hybridizing to a sense or antisense sequence of a gene or naturally occurring mutants thereof, or 5' or 3' flanking sequences or intronic sequences naturally associated with the subject genes or naturally occurring mutants thereof The nucleic acid of a cell is rendered accessible for hybridization, the probe is contacted with the nucleic acid of the sample, and the hybridization of the probe to the sample nucleic acid is detected. Such techniques may be used to detect lesions or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region. In a preferred embodiment of the invention, several probes capable of hybridizing specifically to allelic variants are attached to a solid phase support, for example, a "chip." Mutation detection analysis using these chips comprising oligonucleotides, also termed "DNA probe arrays" is described, for example, by Cronin, et al., (Human Mutation 7:244, 1996). In one embodiment, a chip may comprise all the allelic variants of at least one polymorphic region of a gene. The solid phase support is then contacted with a test nucleic acid and hybridization to the specific probes is detected. Accordingly, the identity of numerous allelic variants of one or more genes may be identified in a simple hybridization experiment.

In certain embodiments, detection of the lesion comprises utilizing the probe/primer in a polymerase chain reaction (PCR) (see, e.g., U.S. Pat. Nos. 4,683,195 and 4,683,202), such as anchor PCR or RACE PCR, or, alternatively, in a ligase chain reaction (LCR) (see, e.g., Landegran, et al., Science 241:1077-1080, 1988; Nakazaw, et al., Proc. Natl. Acad. Sci. USA 91:360-364, 1994), the latter of which can be particularly useful for detecting point mutations in the gene (see, e.g., Abravaya, et al., Nuc. Acid Res. 23:675-682, 1995). In an illustrative embodiment, the method includes the steps of (i) collecting a sample of cells from a patient, (ii) isolating nucleic acid (e.g., genomic, mRNA, or both) from the cells of the sample, (iii) contacting the nucleic acid sample with one or more primers which specifically hybridize to a nucleic acid sequence under conditions such that hybridization and amplification of the nucleic acid (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, et al., Proc. Natl. Acad. Sci. USA 87:1874-1878, 1990), transcriptional amplification system (Kwoh, et al., Proc. Natl. Acad. Sci. USA 86:1173-1177, 1989), Q-Beta Replicase (Lizardi, et al., Bio/Technology 6:1197, 1988), or any other nucleic acid amplification method, followed by the detection of the amplified molecules using techniques well known to those of skill in the art. These detection schemes are especially useful for the detection of nucleic acid molecules if such molecules are present in very low numbers.

Predictive Assays

Laboratory-based assays, which can predict clinical benefit from a given anti-cancer agent, will greatly enhance the clinical management of patients with cancer. In order to assess this effect, a biomarker associated with the anti-cancer agent may be analyzed in a biological sample (e.g., tumor sample, plasma) before, during, and following treatment.

For example, the expression of HER-2, EGFR, VEGF, u-PA, p-PAI-1, and soluble forms thereof, mRNA and protein may be detected in plasma. Thus, changes in the baseline plasma concentration of HER-2, EGFR, VEGF, u-PA, p-PAI-1, and soluble forms thereof, may be monitored in patients with cancer. Additionally, HER-2, EGFR, VEGF, u-PA, p-PAI-1, and soluble forms thereof, protein levels may also be monitored by quantitative immunohistochemistry using paraffin-embedded tumor biopsies.

Another approach to monitor treatment is an evaluation of serum proteomic spectra. Specifically, plasma samples may be subjected to mass spectroscopy (e.g., surface-enhanced laser desorption and ionization) and a proteomic spectra may be generated for each patient. A set of spectra, derived from analysis of plasma from patients before and during treatment, may be analyzed by an iterative searching algorithm, which can identify a proteomic pattern that completely discriminates the treated samples from the untreated samples. The resulting pattern may then be used to predict the clinical benefit following treatment.

Global gene expression profiling of biological samples (e.g., tumor biopsy samples, blood samples) and bioinformatics-driven pattern identification may be utilized to predict clinical benefit and sensitivity, as well as development of resistance to an anti-cancer agent. For example, RNA isolated from cells derived from whole blood from patients before and during treatment may be used to generate blood cell gene expression profiles utilizing Affymetrix GeneChip technology and algorithms. These gene expression profiles may then predict the clinical benefit from treatment with a particular anti-cancer agent.

Analysis of the biochemical composition of urine by 1 D $^1$H-NMR (Nuclear Magnetic Resonance) may also be utilized as a predictive assay. Pattern recognition techniques may be used to evaluate the metabolic response to treatment with an anti-cancer agent and to correlate this response with clinical endpoints. The biochemical or endogenous metabolites excreted in urine have been well-characterized by proton NMR for normal subjects (Zuppi, et al., Clin Chim Acta 265:85-97, 1997). These metabolites (approximately 30-40) represent the by-products of the major metabolic pathways, such as the citric acid and urea cycles. Drug-, disease-, and genetic-stimuli have been shown to produce metabolic-specific changes in baseline urine profiles that are indicative of the timeline and magnitude of the metabolic response to the stimuli. These analyses are multi-variant and therefore use pattern recognition techniques to improve data interpretation. Urinary metabolic profiles may be correlated with clinical endpoints to determine the clinical benefit.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Example 1

Expression Profiling Protocol for Whole Blood Samples

A. Total RNA Isolation from Human Whole Blood

This procedure utilizes the Qiagen QIAamp RNA Blood Mili kit (Version 01/99, QIAamp RNA Mini Protocol for Isolation of Total Cellular RNA from Whole Human Blood).

Tubes of whole blood were stored in a −80° C. freezer. The blood samples were partially thaw on ice, that is, thawed until the blood was an icy slurry which will move freely when the tube is inverted. Three volumes of ice-cold Buffer EL was added to one volume of whole blood in a 50-ml conical tube. The samples were mixed by gentle inversion several times, and the samples were placed on ice. The samples were incubated on ice for 10 minutes with gentle inversion during incubation. The samples were then centrifuged for 10 minutes at 1000 rpm in a tabletop centrifuge at 4° C. The supernatant was decanted, and the sample pellets were placed on ice. One volume of ice-cold Buffer EL was added to the samples, and the samples were gently swirled to resuspend the lymphocyte cell pellet. The samples were transferred to a 15-ml conical tube and placed on ice. An additional 0.5 volume of ice-cold Buffer EL was used to rinse the 50-ml tube, and the rinse was added to the samples. The samples were then centrifuged for 5 minutes at 1000 rpm in a tabletop centrifuge at 4° C.

The supernatant was carefully removed, and 580 µl Buffer RLT (containing B-ME) was added to the cell pellets. The samples were then vigorously vortexed to solubilize the cell pellets. At this point, the samples may be stored at in a −80° C. freezer, or the isolation protocol may be continued with Step 7 of the Qiagen protocol.

The samples were subjected to an on-column DNase digestion using a Qiagen RNase-Free DNase Set. The columns were washed both before and after the digest with 500 µl Buffer RW1, and during the digest, the samples were incubated for 30 minutes at room temperature. Optional Step 12 of the Qiagen protocol was also performed. RNA was eluted with RNase-Free water. Forty-four microliters (44 µl) of RNase-Free water was added directly to the filter, allowed to set for 1 minute, and then centrifuged for 1 minute at $\geq$10,000 rpm. The samples of eluted blood RNA were stored at −80° C. (or the samples may be used immediately).

B. Hybridization of Microarrays

Samples were reverse transcribed to double-stranded cDNA using the Gibco Superscript II Choice System for RT-PCR according to vendor protocol (Invitrogen, CA).

Samples were organically extracted and ethanol precipitated. Approximately 1 µg cDNA was then used in an in vitro transcription reaction incorporating biotinylated nucleotides using an RNA labeling kit (Enzo Diagnostics, NY). The resulting cRNA was put through an RNeasy clean-up protocol and then quantified using UV spectrophotometry. The cRNA (15 µg) was fragmented in the presence of MgOAc and KOAc at 94° C. Fragmented RNA (10 µg) was loaded onto each array, one cRNA sample per array. Arrays were hybridized for 16 hours at 45° C. rotating at 60 rpm in an Affymetrix GeneChip Hybridization Oven 640.

C. Data Analysis

Following hybridization, arrays were stained with Phycoerythrin-conjugated Streptavidin, placed in an Agilent GeneArray Scanner and then exposed to a 488 nm laser, causing excitation of the phycoerythin. The Microarray Suite 5.0 software digitally converts the intensity of light given off by the array into a numeric value indicative of levels of gene expression.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

I claim:

1. A method for monitoring the response of a patient being treated for breast cancer by administering sorafenib in determining the course of therapeutic treatment, said method for monitoring comprising the steps of:
   (a) determining the level of expression of one or more biomarker(s) in a first biological sample taken from the patient prior to treatment with sorafenib;
   (b) determining the level of expression of the one or more biomarker(s) in at least a second biological sample taken from the patient subsequent to the initial treatment with sorafenib; and
   (c) comparing the level of expression of the one or more biomarker(s) in the second biological sample with the level of expression of the one or more biomarker(s) in the first biological sample;
   wherein a change in the level of expression of the one or more biomarker(s) in the second biological sample compared to the level of expression of the one or more biomarker(s) in the first biological sample as compared to statistically valid changes in the baseline level of expression of the biomarker(s) in other patients showing an effective response to sorafenib indicates the effectiveness or lack thereof of the treatment with sorafenib,
   wherein said one or more biomarker(s) is HER-2, EGFR, and soluble forms thereof, and
   wherein
      higher levels of expression of HER-2 or a soluble form thereof indicates a poorer prognosis, and
      higher levels of expression of EGFR or a soluble form thereof indicates a better prognosis.

2. The method of claim 1, wherein said first biological sample and said second biological sample are each a blood, urine, bone marrow or biopsy sample.

3. A method of determining the course of therapeutic treatment for a subject having a breast cancer, comprising:
   administering effective amounts of sorafenib to a subject having high baseline levels of soluble EGFR,
   determining the change in the level of expression of soluble EGFR in said subject from the high baseline levels of soluble EGFR;
   comparing the change from baseline in the level of expression of soluble EGFR in said subject with changes from baseline in levels of expression of soluble EGFR in other patients having a clinically beneficial response to sorafenib to predict the clinical benefit of continuing the administration of effective amounts of sorafenib and
   using said prediction to determine whether to continue the administration of effective amounts of sorafenib for said subject having a breast cancer,
   wherein higher levels of expression of soluble EGFR indicate a better prognosis.

4. A method of claim 1, wherein a change in the level of expression of one or more biomarker(s) in the second biological sample compared to the level of expression of one or more biomarker(s) in the first biological sample predicts the response of the patient to sorafenib.

* * * * *